United States Patent [19]

Chmiel

[11] 4,124,992
[45] Nov. 14, 1978

[54] METHOD AND APPARATUS FOR THE DEEP COOLING OF LIQUID BIOLOGICAL SUBSTANCES

[75] Inventor: Horst Chmiel, Leonberg, Germany

[73] Assignee: Linde Aktiengesellschaft, Wiesbaden, Germany

[21] Appl. No.: 752,836

[22] Filed: Dec. 21, 1976

[30] Foreign Application Priority Data

Dec. 22, 1975 [DE] Fed. Rep. of Germany ....... 2557871

[51] Int. Cl.² .......................... C12B 3/00; F25C 1/00
[52] U.S. Cl. ......................................... 62/74; 195/1.8; 239/424; 424/101; 366/176
[58] Field of Search ..................... 62/347, 74; 195/1.8; 424/101; 239/424; 259/4 R

[56] References Cited

U.S. PATENT DOCUMENTS

| | | | |
|---|---|---|---|
| 2,593,096 | 4/1952 | Brusdal | 239/424 |
| 3,228,838 | 1/1966 | Rinfret et al. | 62/347 X |
| 3,246,883 | 4/1966 | Ashbrook | 259/4 R |

*Primary Examiner*—William E. Wayner
*Attorney, Agent, or Firm*—Karl F. Ross

[57] ABSTRACT

A system for preparing liquid biological substances, such as blood, blood components or cell suspensions for deep freezing which comprises atomizing a protective additive and dripping the biological substance into the stream of the atomized protective substance which is then collected in a receptacle and deep frozen. The system provides an effective way of intimately mixing the protective substance with the biological material to ensure a homogeneous distribution of the protective agent therein.

13 Claims, 6 Drawing Figures

METHOD AND APPARATUS FOR THE DEEP COOLING OF LIQUID BIOLOGICAL SUBSTANCES

FIELD OF THE INVENTION

The present invention relates to a process and an apparatus for the preparation of liquid biological substances, such as blood, blood components, or cell suspensions for deep freezing and, more particularly, for the intimate mixng of the biological substances, prior to freezing, with a protective additive.

BACKGROUND OF THE INVENTION

The preservation of biological substances to prevent irreversible cell damage involves a difficult problem, especially where the conservation of blood is concerned.

For some time, the preservation of blood has been practiced, by conventional techniques, inter alia by deep freezing and storage in liquid nitrogen. This technique permits the long-term storage of blood. A necessary precaution for the successful deep freezing of blood is, however, the admixing therewith of protective additives. Otherwise, when the temperature of the blood passes through the freezing range, the red blood cells are damaged and the cells are hemolized. So that, upon thawing of the preserved blood, it is not necessary to wash out the additives prior to use intransfusion, additives which are inocuous to the human organism, e.g. HES (hydroxyethyl starch), are used.

One of the problems which arise in the preparation of the blood for the freezing process is that of mixing as quickly and completely as possible the additive with the blood, since the cell-survival rate increases with increasing speed of introduction of the additive into the blood. This rate depends upon the penetration of the additive into and its deposition upon the cell membranes.

Furthermore, it is also necessary to ensure that all cells of the suspension have a closely as possible the same concentration of protective additive. Previous processes which have mixed blood and protective additives of the type described above by shaking have resulted in inhomogeneities which give rise to a high degree of damage to the red blood corpuscles during the freezing process.

OBJECTS OF THE INVENTION

It is the principal object of the present invention to provide a process for the mixing of biological substance and protective additives and the packing of the resulting mixture for deep freezing whereby an improvement in the degree of mixing can be obtained at low cost and in such fashion as will permit a supply of the protective additive at high speeds and in the closest possible uniform concentration to the biological substance.

Another object of the invention is to provide an apparatus for effectively accomplishing the improved process.

It is still another object of the invention to provide a method of and an apparatus for the deep freezing of blood, blood components and cell suspensions which eliminates the drawbacks enumerated above.

SUMMARY OF THE INVENTION

These objects and others which will become apparent hereinafter are attained, in accordance with the present invention, in a system whereby the protective additive is atomized and the biological substance is introduced into the atomized stream in droplets, the resulting mixture being collected in a receptacle and deep frozen.

Wherever deep freezing is described below it is to be understood that the same is preferably carried out by the method and with the apparatus described in my concurrently filed application Ser. No. 752,930, commonly assigned with the present case. This application is incorporated herein in its entirety by reference, not only with respect to the specific deep-freezing techniques, but also with respect to the additives described therein and the cell suspensions which are processed by the deep freezing approach.

The present invention is based upon my discovery that the mixing of two liquid media is effected most efficiently for the combination of protective agents and biological substances when the relative amounts of the protective agent and the biological substance are substantially constant at all time during the mixing process and the speed of assimilation of the protective substance into the bilogical substance is at a maximum. The mixing of two liquid media has the characteristic that the mixing speed is proportional to the contact surface of the two media, i.e. to the interfacial surface area. This means that the greatest possible surface area for the prescribed volume should be obtained so that the volume units of the media upon combination should be as small as possible.

According to the invention this is attained by subdividing the liquid protective agent as finely as possible, i.e. by atomizing it by ultrasonic means, and by causing the contact between the atomized particles of the protective agent to come into contact with a subdivided biological substance, i.e. droplets thereof.

When the protective additive or agent is atomized before the biological substance is introduced in the form of droplets thereto, the protective additive has the largest possible contact surface (specific surface area) while the individual droplets of the protective additive also have a high surface energy by comparison to the non-atomized volume. These droplets or particles tend to combine readily with other fluid particles to minimize their surface energy. Hence, they tend to agglomerate upon and coalesce with the particles or droplets of the biological substance. Finally, in this connection, since the atomized stream has a high kinetic energy, this kinetic energy serves to ensure a homogeneous mixing of the two media.

It has been found, according to a highly advantageous feature of the invention, that it is possible to atomize the protective agent by means of a pump at a high pressure of, for example, 160 bars and thereupon spraying the protective agent at this high pressure from a nozzle. Best results are obtained when the biological substance is, in this case, introduced into the center of the atomized stream.

The use of the pump provides an excellent ability to deliver the protective agent in predetermined quantities, i.e. a well-defined dosing of the protective agent, since with each working stroke of the pump at a uniform speed, the protective agent is delivered in precisely defined quantities.

The pump-generated high pressure also serves to atomize the spray relatively viscous fluids as are often used as protective agents. This is of considerable significance since the protective agent should be added to the biological substance in the highest possible concentration so that an excessive volume of the protective agent will not be supplied to the biological substance. Furthermore, with higher concentrations the surface tension is lower and a better mixing of the two media can be obtained.

According to another aspect of the invention, the protective agent is atomized with the aid of a pressurized carrier gas which can have a relative low superatmospheric pressure of, for example, 0.5 to 1 bar even when viscous fluids are to be entrained in the atomized stream. The control of the kinetic energy of the atomized stream can be accomplished with any given atomizing nozzle in a simple manner by the use of a supply valve in the feed line for the protective additive or the carrier gas. In this case a lateral dripping of the biological substance into the atomized stream can be effected with excellent mixing of the two media.

The carrier gas is preferably nitrogen since this gas does not effect either the chemical composition of the protective agent or the components of the biological system in a disadvantageous manner. If, in addition, the carrier gas is passed through a filter prior to its used in atomizing the liquid protective agent, e.g. a membrane filter, the infecting of the biological substance by microorganisms contained in the gas can be avoided.

An apparatus for carrying out the process of the present invention can advantageously comprise replaceable supply vessels for the biological substance and for the protective agent, a nozzle unit capable of atomizing the protective agent, and means for feeding the biological substance and the protective agent to the nozzle. The two supply vessels can be disposed at a higher level than the nozzle unit and can be connected thereto via separate lines and control elements such as valves or the like, whereby the two liquids flow by gravity to the nozzle. The supply of the protective agent and the biological substance can be controlled independently and a desired ratio of the feed of the two can be established with ease. The replaceability of the supply vessels permits both the protective agent and the biological substance to be packaged in sterile units and to be connected to the respective supply lines in a sterile manner. Of course, all or part of the apparatus can be contained in a sterile sealed chamber to avoid infection of the biological substance by microorganisms in the environment.

According to one aspect of the invention, the line from the supply vessel for the protective agent to the nozzle unit can include a pump in which the protective agent is brought to the abovementioned high pressure prior to atomizing. With the use of this pressure, the protective agent is fed to the nozzle unit and atomized therein. It has been found to be most desirable to carry out the atomizing in a nozzle arrangement having a annular gap for the protective agent and means whereby the biological substance can be introduced into the center of the atomized stream at the end thereof emerging from the annular gap. The nozzle can have a central passage for introducing the biological substance into the atomizing stream in this embodiment of the invention.

When the protective agent is to be atomized with a carrier gas, the nozzle unit can be connected to a nitrogen bottle via a pressure-measuring device and a filter. The pressure-measuring device permits the establishment of a predetermined desired velocity and flow rate of the carrier gas into the nozzle so that a high uniform gas velocity is ensured.

Because of the construction of the atomizing nozzle unit in the latter embodiment, the protective agent is preferably introduced to the carrier gas through a central passage while the carrier gas is fed through the annular gap. At the annular gap the protective additive is entrained in an atomized stream. In this case the biological substance is fed laterally of the nozzle into the atomized stream at a constant rate from its supply nozzle in droplets.

When the carrier gas is fed at a uniform flow velocity and the protective agent is fed to the carrier gas at a constant rate, an excellent mixing of the protective agent with the biological substance is obtained with constant concentration conditions, i.e. the concentration of the protective agent in the biological substance remains constant.

According to a further feature of the invention, clamping means, e.g. a clamping ring, band or the like, is provided to affix the upwardly open synthetic-resin sack forming the receptacle for the mixture containing the biological substance to the atomizing nozzle unit, whereby the sack hangs detachably therefrom and can receive the preserved blood. After the filling process is complete, the synthetic-resin sack is thermally or ultrasonically welded closed and is supplied to a deep-freeze apparatus of the type described in the aforementioned copending application.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
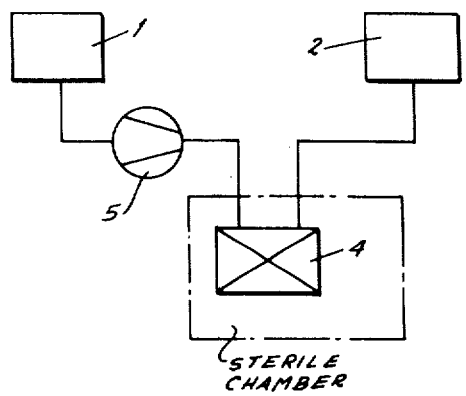
FIG. 1 is a flow diagram illustrating an apparatus for the mixing of biological substances and protective agents with the aid of a pressurizing pump.

FIG. 1 shows an apparatus for the mixing of a biological substance with a protective agent in a sterile-sealed chamber represented only diagrammatically by dot-dash lines in FIG. 1 and which contains at least the nozzle unit 4. The nozzle unit 4 has been shown in greater detail in FIG. 2.

The nozzle unit 4 is connected via separate ducts or tubes with respective supply vessels 1 and 2 for the protective agent and the biological substance.

Figure 5:
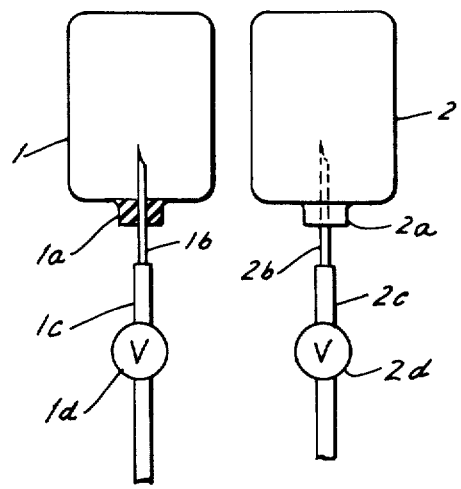
FIG. 5 is a diagrammatic elevational view of the container assembly for use in the system of either FIG. 1 or FIG. 3.

As can be seen from FIG. 5, the vessels 1 and 2 are replaceable and can be provided with self-sealing outlets 1a and 2a which can be penetrated by needles 1b and 2b of the respective feed lines 1c and 2c running to the nozzle unit 4. The tubes 1c and 2c may be of the flexible-wall type and can be provided with respective valves 1d and 2d for controlling the rates of flow of the biological substance and the protective agent to the nozzle unit. The valves can be of the pinch type or any other (e.g. Hofmann clamp) commonly used in blood processing.

The vessels 1 and 2 are thus stored under sterile conditions and are merely inserted onto the respective needles, being supported by conventional means, suitable venting being provided, to deliver the respective liquids in a sterile manner to the atomizing unit.

In the line running from the supply vessel 1 for the protective agent to the atomizing unit 4, there is provided a pump 5 capable of generating the aforementioned elevated pressure of about 160 bars. The pump 5 can be of the constant-displacement type wherein each stroke of the pump delivers a predetermined quantity of the protective agent.

Figure 2:
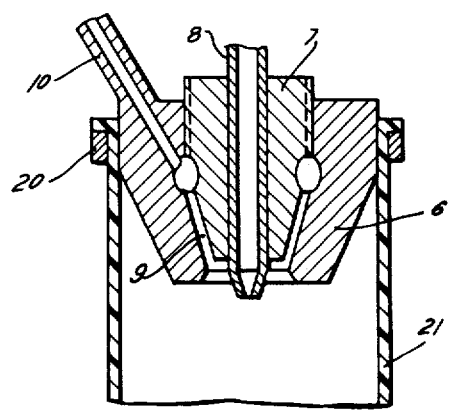
FIG. 2 is a detail axial-cross-sectional view, partly in diagrammatic form, of an atomizing nozzle for the system of FIG. 1.

As can be seen from FIG. 2, the nozzle unit comprises a nozzle body 6 into which is threaded a central member 7 defining a frustoconically-converging annular gap 9 which opens at the mouth of the nozzle. The insert 7 carries the tube 8 through which the biological substance is fed, the tube 8 opening centrally within the atomized stream produced when the liquid protective agent emerges at high pressure from the annular gap 9. The latter terminates short of the smallest diameter portion of the nozzle for most effective atomization. A passage 10 in the housing 6 connects the annular gap 9 with the supply vessel 1 for the protective agent via the pump.

Figure 3:
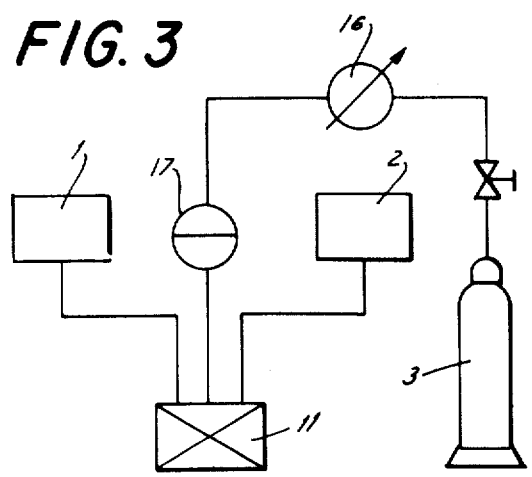
FIG. 3 is a view similar to FIG. 1 of an apparatus for the mixing of biological substances and protective agents with the aid of a carrier gas.

The mixing apparatus illustrated in FIG. 3 differs from that of FIG. 1 in that the nozzle unit 11 for producing the atomized stream of the protective agent is connected in addition to a pressurized-gas bottle 3 containing the carrier gas. The carrier gas is preferably nitrogen under elevated pressure. In this case the pump for the protective agent can be eliminated. The carrier gas is supplied from the bottle 3 to the nozzle unit 11 via a membrane filter 17 which removes microorganisms which are capable of infecting the biological substance. A pressure controller 16 is also provided. The supply vessels 1 and 2 are connected via the aforementioned valves to the nozzle unit 11 separately as will be described in greater detail in connection with FIG. 4. With a constant pressure at the regulator 16 the flow velocity of the carrier gas into the nozzle unit is determined and, since the drops of the biological substance and the flow rate of the protective agent can be well defined by the use of the valves 1d and 2d, completely constant mixing conditions are maintained in the nozzle 11 and a rapid and uniform mixing of the two media is obtained.

Figure 4:
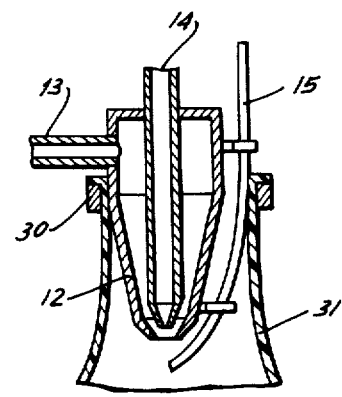
FIG. 4 is a view similar to FIG. 2 of a nozzle unit for the system of FIG. 3.

FIG. 4 shows the nozzle unit 11 in greater detail. The nozzle unit 11 thus comprises a conically-converging nozzle body 12 into which a tube 14 extends centrally and terminates ahead of the nozzle end from which the atomized stream emerges. The protective agent is supplied to the central tube 14 and the carrier gas is fed to the space surrounding this tube via a lateral fitting 13. Attached to the nozzle body 12, moreover, is a laterally extending supply tube 15 from which the biological substance is fed in droplets to the atomizing stream at the point at which the latter is sprayed from the nozzle.

In FIGS. 2 and 4, moreover, I have shown clamping elements 20 and 30 whereby the synthetic-resin sacks 21 and 31 collecting the blood mixture can be attached to the nozzle units. When these clamps are released, the sack can be removed and sealed for transfer to the deep-freezing unit fully described and illustrated in the aforementioned copending application.

By way of example, the protective agent can be an aqueous solution of hydroxyethylstarch, high molecular Dexhan, gelatin or polyvinylpyrrolidone. An 87% aqueous glycerine solution having a viscosity of 145 cP $\triangleq$ 0.145 Ns/m$^2$ is used and the other protection agents can be used if provided in the same viscosity with precisely the same effect.

The biological substance treated was normal human blood and the protective agent was fed at a velocity of 216 cm/sec which, for a nozzle diameter of 0.07 cm corresponded to a volume rate of flow of 0.83 cm$^3$ per second. The pressure of the carrier gas was between 0.5 and 1 atmosphere (gauge), generally approximately 1 bar, and was first passed through a membrane filter for mechanical sterilization.

The particle size in the atomized stream amounted to less than 0.1 mm and the angle of spread (apex angle) of the stream was about 60°. The droplets of the biological material were introduced in a particle size of about 2 mm and the concentration of the protective agent in the collected material was found to be about 15% under the conditions given above.

Figure 6:
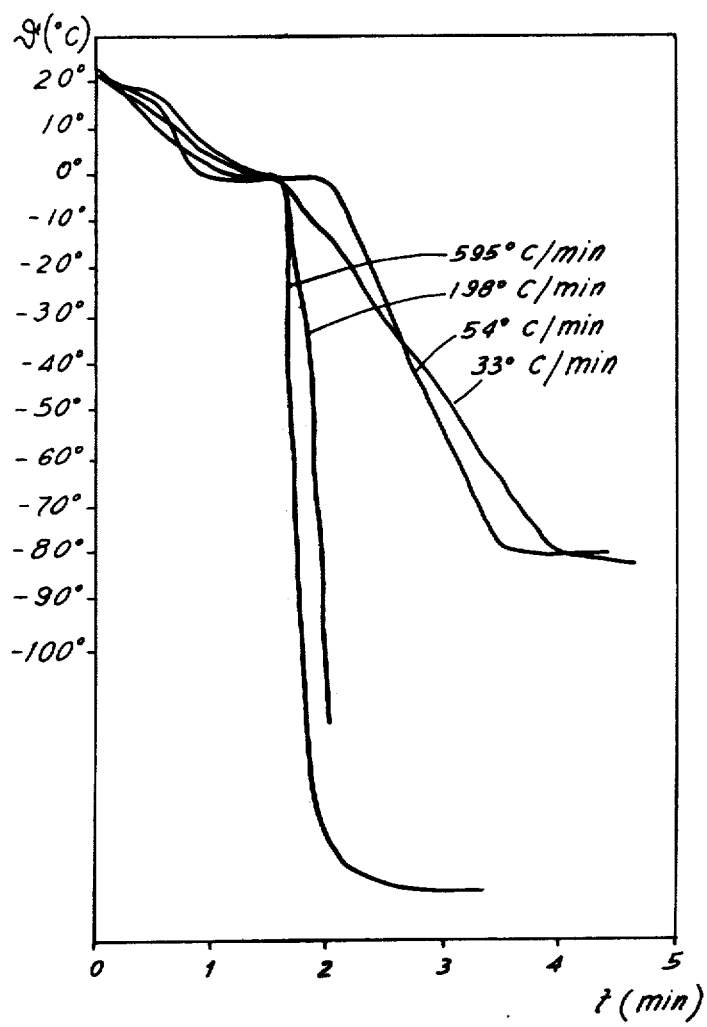
FIG. 6 is a graph illustrating the invention.

The collected mixture was subjected to freezing at varying conditions as illustrated in FIG. 6 which shows the freezing temperature in degrees centigrade plotted along the ordinate, the time in minutes plotted along the abscissa and the freezing rates or slopes. Best results were obtained at the rate of 595° C. per minute. The freezing time from 0° C. to the minimum temperature of −196° C. was about 2 minutes. It was found that best results were obtained when the temperature was always held at around −196° C. after the freezing operation. In all cases, the survival of red blood cells was better than 98%.

I claim:

1. A process for mixing a liquid biological substance such as blood, blood components and cell suspensions, with a liquid protective agent stabilizing the biological substance for subsequent deep freezing, said process comprising the steps of:
    atomizing said protecting agent in an atomized stream;
    dripping the biological substance in droplets into said stream, thereby mixing the biological substance with the protective agent and forming a mixture thereof; and
    collecting said mixture in a container.

2. A process for the deep freezing of a liquid biological substance which comprises:
    mixing said biological substance with a protective agent as defined in claim 1 and collecting the resulting mixture in said receptacle; and
    deep freezing the mixture in said receptacle.

3. The process defined in claim 1 wherein said protective agent is subjected to an elevated pressure and is sprayed from a nozzle to form said atomized stream, said biological substance being dripped into the center of said atomized stream.

4. The process defined in claim 1 wherein said protective agent is atomized by entrainment in a carrier gas in an atomizing nozzle.

5. The process defined in claim 4 wherein said carrier gas is nitrogen, said process further comprising the step of passing said carrier gas through a filter to remove microorganisms therefrom.

6. An apparatus for mixing a liquid biological substance such as blood, blood components and cell suspensions with a protective agent capable of stabilizing the biological substance upon the deep freezing thereof, said apparatus comprising:
- a first supply vessel for said protective agent;
- a second supply vessel for said biological substance;
- an atomizing nozzle unit;
- respective ducts connecting each of said supply vessels separately with said nozzle unit;
- said nozzle unit being adapted to atomize said protective agent and form an atomized stream therefrom and said biological substance is dripped in droplets into said stream; and
- means for collecting the mixture of the droplets of biological substance and atomized protective agent formed in said stream.

7. The apparatus defined in claim 6 further comprising a pump in the duct connecting said first supply vessel with said nozzle unit, said nozzle unit transforming said protective agent under high pressure into atomized particles of said agent.

8. The apparatus defined in claim 7 wherein said nozzle unit comprises:
- a nozzle body having a frustoconically-converging passage terminating at a mouth of said body;
- an insert threaded into said body and defining a frustoconically-convergent annular gap therewith;
- means for feeding said agent from said pump at high pressure into said gap whereby said agent emerges at said mouth in an atomized stream;
- a tube extending through said insert and opening into the center of said stream, said tube being connected to the duct of said second vessel.

9. The apparatus defined in claim 6 further comprising:
- a source of a carrier gas under pressure; and
- means connecting said source with said nozzle unit whereby said carrier gas entrains said agent from said nozzle unit in an atomized stream.

10. The apparatus defined in claim 9 wherein said nozzle unit comprises: a conically-convergent nozzle provided with a fitting connected to said source;
- a central tube opening into said nozzle and supplying same with said protective agent; and
- a further tube extending laterally into said stream and connected to said second vessel for dripping said biological substance into said stream.

11. The apparatus defined in claim 10 further comprising between said fitting and said source, a pressure controlling unit for regulating the pressure of the carrier gas delivered to said nozzle unit and a filter for removing microorganisms from said carrier gas prior to its introduction into said nozzle unit.

12. The apparatus defined in claim 6, further comprising means for removably retaining said receptacle on said nozzle unit.

13. The process defined in claim 1 wherein said protective agent is atomized by ultrasonics.

* * * * *